United States Patent [19]
Henry

[11] Patent Number: 5,893,275
[45] Date of Patent: Apr. 13, 1999

[54] COMPACT SMALL VOLUME LIQUID OXYGEN PRODUCTION SYSTEM

[75] Inventor: Charles W. Henry, Denver, Colo.

[73] Assignee: In-X Corporation, Lakewood, Colo.

[21] Appl. No.: 08/923,608

[22] Filed: Sep. 4, 1997

[51] Int. Cl.[6] .................................................. F25J 1/00
[52] U.S. Cl. .......................... 62/615; 62/6; 62/616; 62/911
[58] Field of Search ................. 62/615, 616, 911, 62/6

[56] References Cited

U.S. PATENT DOCUMENTS

| | | | |
|---|---|---|---|
| Re. 19,031 | 12/1933 | Heylandt | 62/1 |
| 2,919,555 | 1/1960 | Hughes et al. | 62/13 |
| 3,714,942 | 2/1973 | Fischel et al. | 128/142 |
| 4,017,284 | 4/1977 | Gifford | 62/911 |
| 4,211,086 | 7/1980 | Leonard et al. | 62/50 |
| 4,561,287 | 12/1985 | Rowland | 73/23 |
| 4,583,364 | 4/1986 | Wood | 60/520 |
| 4,587,967 | 5/1986 | Chu et al. | 128/204 |
| 4,602,174 | 7/1986 | Redlich | 310/15 |
| 5,060,480 | 10/1991 | Sauliner | 62/616 |
| 5,144,945 | 9/1992 | Nishino et al. | 128/205 |
| 5,342,176 | 8/1994 | Redlich | 417/212 |
| 5,388,413 | 2/1995 | Major et al. | 62/911 |
| 5,461,859 | 10/1995 | Beale et al. | 60/517 |
| 5,496,153 | 3/1996 | Redlich | 417/212 |
| 5,499,623 | 3/1996 | Pasternack | 128/201 |
| 5,525,845 | 6/1996 | Beale et al. | 310/30 |
| 5,558,139 | 9/1996 | Snyder | 141/95 |

*Primary Examiner*—Ronald Capossela
*Attorney, Agent, or Firm*—Sheridan Ross P.C.

[57] ABSTRACT

The compact oxygen production system of the present invention provides an oxygen concentrator and a cryocooling device for liquefying the concentrated oxygen gas to provide liquid oxygen. The compact size of the system permits the system to be employed in home applications, especially for home oxygen patients.

24 Claims, 7 Drawing Sheets

# COMPACT SMALL VOLUME LIQUID OXYGEN PRODUCTION SYSTEM

FIELD OF THE INVENTION

The present invention is directed generally to an apparatus for liquefying gases and specifically to a compact, personal oxygen liquefaction system for producing small volumes of liquid and gaseous oxygen on a continuous basis in an oxygen patient's home.

BACKGROUND OF THE INVENTION

A significant number of people, typically elderly, suffer from chronic respiratory insufficiency due to restrictive airway disease, obstructive pulmonary disease, neuromuscular disorders or other complications. Symptoms of chronic respiratory insufficiency includes shortness of breath, weight loss, headaches and sleeplessness.

To alleviate these symptoms, home oxygen is prescribed by a physician and then delivered to the patient by a home healthcare equipment professional. Oxygen is provided to the patient by one of three modalities: (a) liquid oxygen, (b) high pressure oxygen cylinders, or (c) an oxygen concentrator. Each modality has specific disadvantages to either the patient or the home healthcare professional. Modalities (a) and (b), require the oxygen to be periodically replenished by the home healthcare professional. Such refilling procedures are inefficient and therefore costly. Modality (c) does not provide oxygen in a form that allows the patient to be ambulatory, thereby dooming the patient to a sedentary life style. This can not only be psychologically depressing but also frequently causes further degeneration in health because of inactivity.

There is a need for a compact, efficient, low cost, personal system for continuously concentrating and then providing oxygen in either gaseous or liquid form to a home oxygen patient. There is a further need on the part of the home healthcare equipment professional for a cost effective means for providing liquid oxygen to a home oxygen patient which does not require periodic, expensive deliveries of supplemental liquid oxygen.

SUMMARY OF THE INVENTION

These and other needs are addressed by the compact oxygen production system of the present invention. The system includes (a) a separating device for separating oxygen from an input fluid to form a feedstream concentrated to the desired oxygen purity, (b) a refrigeration device, in communication with the separating device, for refrigerating the feedstream to liquefy the oxygen gas component. The system is particularly useful for producing small volumes of liquid oxygen in remote locations, especially the homes of oxygen patients. Unlike conventional large-scale liquid oxygen production plants, which first cryogenically liquefy the input gas and then separate oxygen from other components through a distillation process, this system separates oxygen from the input gas before liquefaction, thereby lessening the refrigeration requirements.

The system can be a free-standing unit having a small enough size that the unit can be accommodated in most home environments. The system may be combined into one unit with the oxygen separating device or it may be utilized as two distinct components. In either the unimodular or bimodular configuration, the system can have a relatively compact size. In one embodiment of the unimodular version, the system may have a height of about 40 inches or less, a width of about 24 inches or less, and a length of about 30 inches or less. In one embodiment of the bimodular version, the refrigeration unit has a height of about 28 inches or less, a width of about 22 inches or less, and a length of no more than 18 inches.

In conventional liquefaction systems, a heat exchanger (to remove the heat of compression and to exchange heat with the effluent waste heat) and a distillation column (to separate the component oxygen) operate either partially (i.e., the heat exchanger) or entirely (i.e., the distillation column) at cryogenic temperatures. This requires a relatively large refrigeration capacity for the liquefaction process and therefore a more expensive system for a given capacity relative to the small design of the present invention. The larger systems are designed to maximize production efficiency and to produce many tons of liquid oxygen per day. They are not designed for personal use. It is not that the proposed system is more efficient or technically superior. It is valuable because net of delivery costs, it produces a lower cost source of liquid oxygen to the patient. Unlike conventional liquefaction systems, the design of the present invention does not require separate equipment to clean impurities from in-flowing fluid which could freeze and clog the system. For the present invention, the cleansing of the feedstream received from the oxygen separation system is performed by the oxygen separation system. This allows the refrigeration module to be small and maintenance free for this procedure.

The system's simple design and utilization of low-cost components create a relatively low-cost yet robust system. The system can produce a continuous flow of liquid oxygen to the home oxygen patient portable breathing system, by making the liquid oxygen in the home. The availability of such liquid oxygen can result in improved patient care of the patient who may have been limited to just gaseous (stationary) sources of oxygen because of the historically high cost of liquid oxygen. The system provides lower cost liquid oxygen, therefore allowing more patients on gaseous oxygen to be ambulatory and to enjoy an improved quality of life.

The design of the separating device can be based on any number of oxygen concentrating techniques, including, but not limited to, any device based on the adsorptive processes (e.g., molecular sieves), membranes, ceramics, and ionic conductors. The system may be connected to any of these technologies by simple oxygen tubing.

The refrigeration device includes a cryocooler and a condensation device in thermal communication with the cryocooler. The resulting liquid product can then be stored in a reservoir or vessel.

To enhance the refrigeration capacity of the cryocooler and therefore increase the production of liquid oxygen from the system, the system can include an additional refrigeration device, such as a conventional refrigerator, for cooling the or near the heat rejection member of the cryocooler. As will be appreciated, the heat rejection member dissipates the heat of the compression of the refrigerating fluid in the cryocooler. Cooling the heat rejection member will result in lowering its temperature, resulting in increased refrigeration capacity for the system at a relatively modest cost.

The system can include bypass valves, located between the separating device and the cryocooler, for removing a portion of the oxygen enriched feedstream. This removed portion would may be used to provide a portion of the oxygen enriched feedstream directly to the patient, or for sampling the oxygen enriched feedstream for monitoring purposes. Accordingly, when the patient is located in the vicinity of the system, he or she can inhale directly the diverted oxygen enriched feedstream, without interrupting the balance of the feedstream flowing to the liquefying portion of the system.

Using the relatively compact system, a method can be provided for producing and storing small volumes of liquid and gaseous oxygen, a feature of particular value to home oxygen patients. This method utilizes the system in the following steps: (a) placing the system at a remote location at which a user of liquid and gaseous oxygen resides; (b) operating the system to produce gaseous and liquid oxygen at the remote location; (c) storing the liquid oxygen portion of the production within the refrigeration portion of the system's internal reservoir and providing the gaseous portion of the production directly to the user; and (d) periodically allowing a small volume of liquid oxygen to be transfilled to the user's ambulatory liquid oxygen container for mobile consumption of gaseous oxygen as the liquid oxygen vaporizes. The supplying of the liquid oxygen to the remote location can be completed free of any delivery of liquid oxygen to the remote location from an external location. The storing step of the liquid oxygen can be conducted using the refrigeration portion of the system. The delivering step can be conducted while the system is operating and does not require additional oxygen from any outside source.

BRIEF DESCRIPTION OF THE DRAWINGS

FIG. 4A is the Carnot cycle, FIG. 4B the Stirling cycle, and FIG. 4C the Brayton cycle;

DETAILED DESCRIPTION

Figure 1:
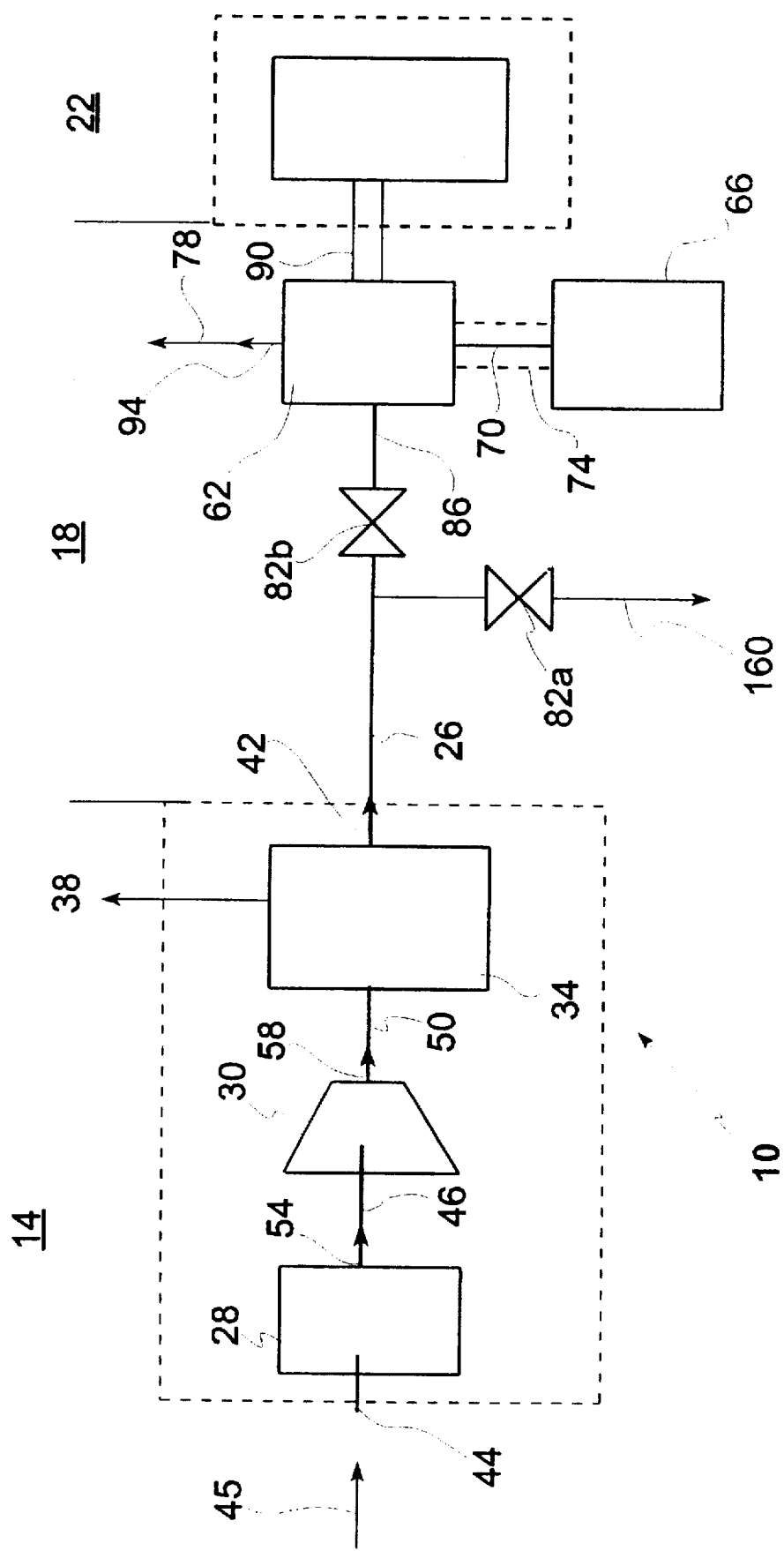
FIG. 1 is a schematic depicting the various components of the compact oxygen production system according to the present invention.

Referring to FIG. 1, the various components of the gaseous and liquid oxygen compact production system 10 are depicted. The system 10 includes a concentrator subsystem 14, a cryogenic subsystem 18, and a cryocooler 22. As depicted in FIG. 1, the concentrator and cryogenic subsystems 14 and 18 are in fluid communication via conduits 26 and 86, and the cryogenic subsystem 18 and cryocooler 22 are in thermal communication. The system 10 is capable of producing not only liquefied oxygen but also liquefied nitrogen, and other gases, and mixtures thereof. For purposes of simplicity, the system 10 is described with specific reference to liquid oxygen production.

The concentrator subsystem 14 includes a filter 28, a compression device 30, and a separator 34. The concentrator subsystem 14 is located upstream of the cryogenic subsystem 18, and it provides the energy necessary for the separator 34 to form a concentrated gas 42, primarily containing molecular oxygen. The concentrated gas 42 preferably contains at least about 70% and more preferably at least about 85% by volume molecular oxygen. The concentrator subsystem 14 produces an offgas 38 and the concentrated gas 42. The offgas 38 can include a variety of components, including nitrogen, carbon dioxide, and water.

The filter 28 in the concentrator subsystem 14 is in fluid communication with a gas input 44 and the compression device 30 via conduit 46 and removes particulate matter from gas, such as air, inputted into the concentrator subsystem 14.

The compression device 30, which is in fluid communication with the separator 34 via conduit 50, compresses the filtered gas 54 to form compressed gas 58. The compression device 30 can be in thermal communication with a heat exchanger (not shown) for effective removal of the heat from the compressed gas 58.

The configuration of the separator 34 depends upon the application. By way of example, the configuration can be based on adsorptive processes, membrane separation, and ionic conduction. In all of the configurations, the separator 34 can include a vacuum pump valves, timers and control and alarm systems (not shown) in addition to the compression device.

In adsorptive processes, the separator 34 includes one or more pressurized vessel(s) containing a gas adsorptive medium, preferably molecular sieves such as zeolites, having pore size and other characteristics as to preferably absorb nitrogen in the compressed gas 58 at a first, higher pressure and later release the component(s) at a second, lower pressure. The first and second pressures are different. The ratio of the maximum first and minimum second pressure is generally in the 3–10 range, and preferably in the 3 to 5 range. The minimum second pressure may be near atmospheric or sub-atmospheric. Accordingly, in a first cycle the air is preferably passed through a bed of molecular sieves at the first pressure adsorbing the nitrogen, water vapor and carbon dioxide and in a second cycle the vessel is purged of the compressed gas and the nitrogen gas and other adsorbates are then released from the bed at the second pressure. The cycles are then repeated. A multiplicity of oppositely cycled adsorbent beds can be used to assure a continuous flow of concentrated gas 42 or a double or single bed with a properly sized accumulator vessel.

In membrane separation, the separator 34 comprises a plurality of membranes. Each of the membranes has a high pressure gas (such as the compressed gas 58 for the first membrane) on an upstream side and low pressure (filtered) gas on a downstream side. In this manner, the oxygen and water vapor in the high pressure gas contacting the upstream side of a membrane pass through the membrane to the low pressure side of the membrane to form the molecular oxygen enriched filtered gas. The high pressure gas has a pressure typically ranging from about 7 to about 14 atm and the low pressure gas a pressure typically ranging from about atmospheric to about 1.5 ATM. It is also possible in membrane separation to reverse the order of the compressor 30 and of the separator 34. In that case the compressor acts as a vacuum pump and provides suction on the low pressure, downstream side where the oxygen enriched gas will be produced. A plurality of membranes connected in series may be required to realize a high level of purity of the molecular oxygen in the concentrated gas 42.

In ionic conduction, the separator 34 includes a conductive membrane and it may include a voltage source for biasing the membrane. Alternately, the driving force may be provided by a pressure difference between the upstream side (conduit 50) and the downstream side (conduit 26) of the high temperature membrane.

Figure 2:
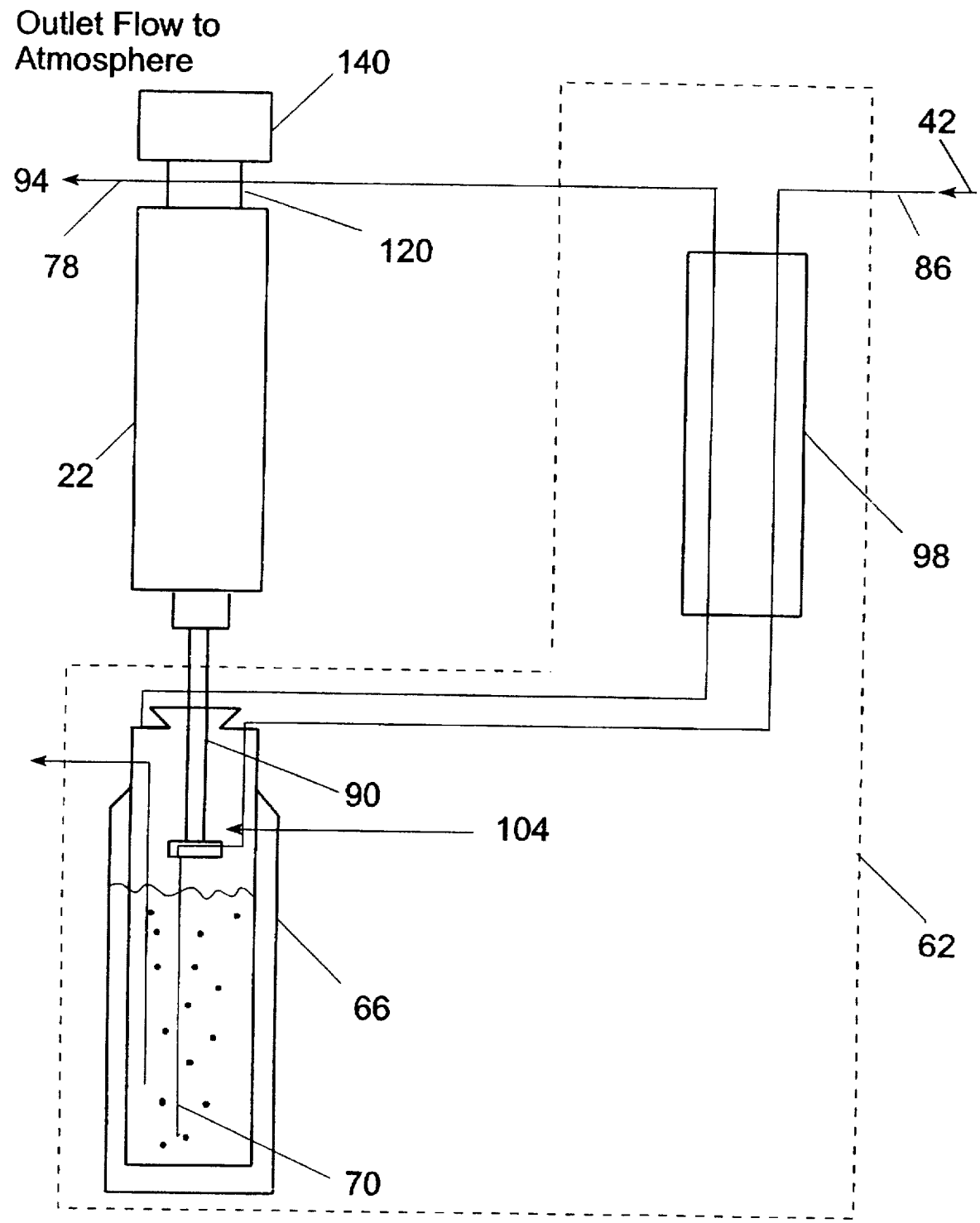
FIG. 2 depicts the components of a portion of the liquefying assembly.

Referring to FIGS. 1 and 2, the cryogenic subsystem 18 includes a liquefier 62 for condensing the concentrated gas 42, a dewar 66 for collecting the liquefied concentrated gas, conduit 70 connecting a condenser 104 of the liquefier 62 and the dewar 66, cryogenic insulation 74 (not shown in FIG. 2) surrounding the conduit 70 and the condenser 104, and a heat exchanger 98 to minimize the loss of refrigeration from the liquefier 62. The conduit 26 has a "T" branching off to bypass valves 82a,b for providing concentrated (but unliquefied) gas to a user or, alternatively, directing a portion of the concentrated gas 42 to the liquefier 62 via conduit 86.

The liquefier 62 is in thermal contact with a cold finger 90 of the cryocooler 22. The cold finger 90 includes a condensation surface as part of the condenser 104 which is cooled to a temperature ranging from about 7° k to about 90° k by the cold finger 90. A waste gas 94 is removed from the liquefier 62.

The heat exchanger 98 can be located along the conduits 86 and 78 to transfer heat from the concentrated gas 42 in the input line 86 to the waste gas 94 in the output line 78.

Figure 3:
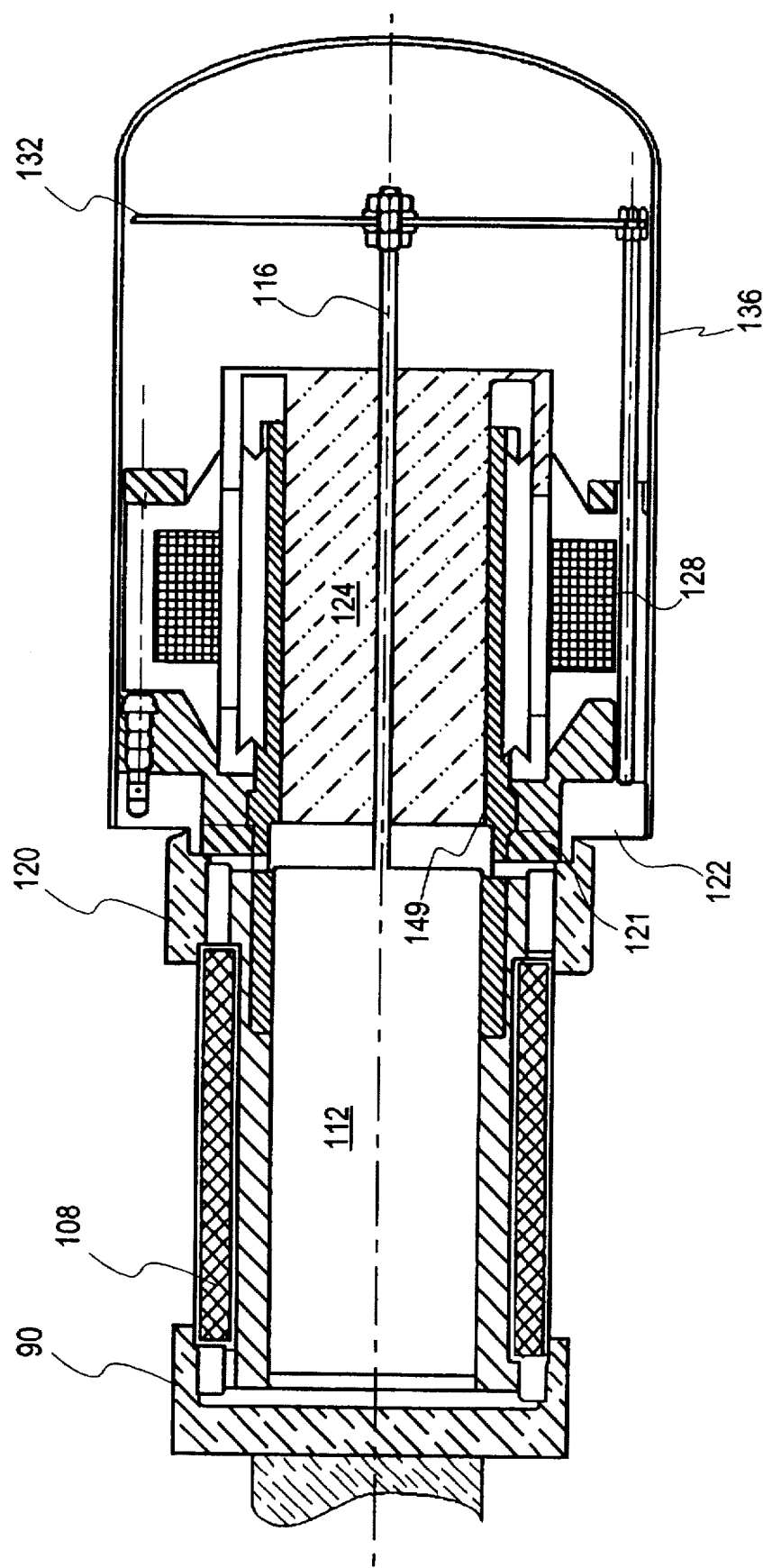
FIG. 3 depicts the components of a linear Stirling type cryocooler.

Referring to FIGS. 1–3, the cryocooler 22 includes a displacer 112, the cold finger 90, which may be placed inside the displacer 112, regenerator 108, cylinder 149 and attached displacer rod 116, heat rejector 120, piston 124, linear motor 128 which alternately may be placed outside of casing 136, for driving the displacer 112 and piston 124, spacer 121, flange 122, and displacer spring 132. To improve the cooling capacity of the cryocooler a separate near ambient temperature refrigeration unit 140 (not shown in FIG. 3) can be positioned over the heat rejector 120 to improve the capacity of the cryocooler 22. The casing 136 may also be cooled by the separate refrigeration unit 140. Preferably, the cryocooler 22 is based on the Stirling cycle depicted in FIG. 4B, the Ericsson cycle (not shown), or magnetocaloric effects.

Figure 4:
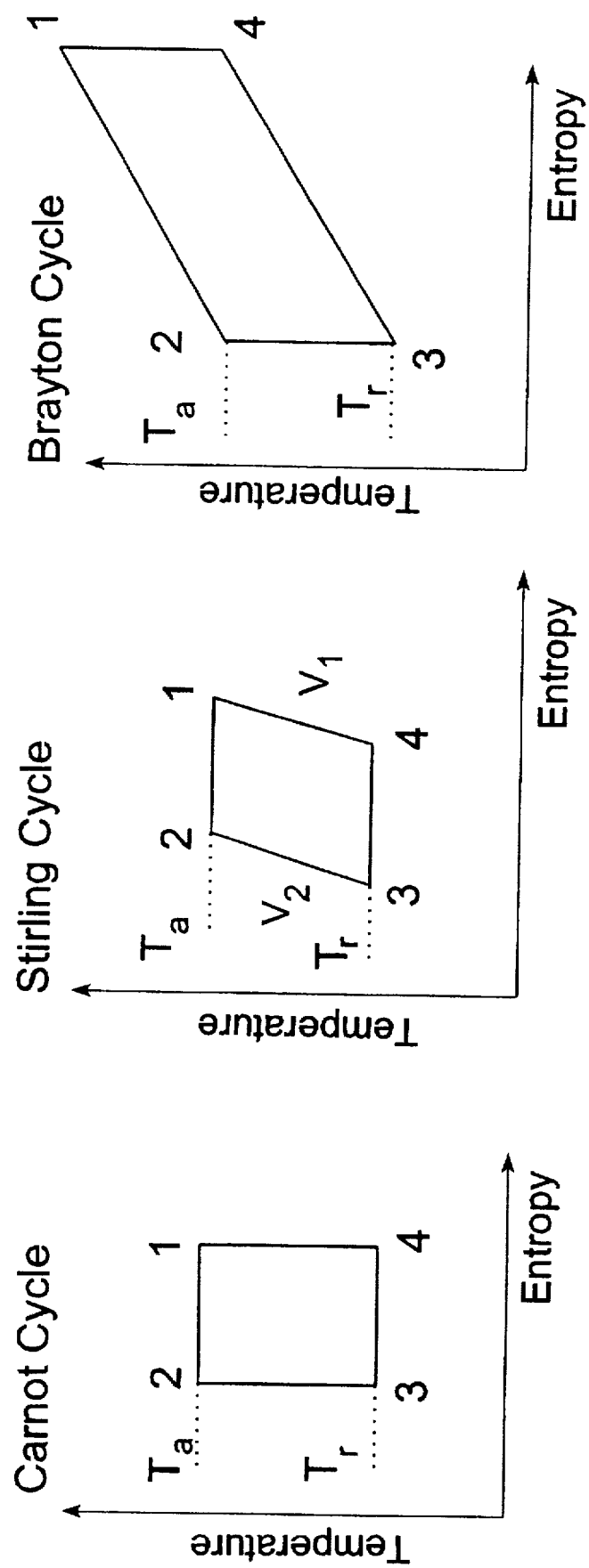
FIGS. 4A–C are plots of entropy vs temperature depicting the different refrigeration cycles, where

Referring to FIG. 4B, the Stirling cycle, which is a preferred thermodynamic cycle, is depicted with reference to the operation of the cryocooler 22. At point "1" the piston 124 is at the maximum displacement relative to the displacer 112 while the displacer 112 is stationary. From points "1" and "2", the piston 124 moves towards the displacer 112, thereby compressing a cooling fluid in the compression space. The compression of the cooling fluid releases a heat of compression, which is thermally dissipated by the heat rejector 120. "$T_a$" denotes the ambient temperature, and "$T_r$" denotes the refrigeration temperature. From points "1" to "2" the ideal Stirling cycle is characterized by constant temperature compression and reversible isothermal heat removal. During the time interval from points "1" to "2", the displacer 112 remains in the same position. From points "2" to "3" the piston 124 moves to a position of full compression and the displacer 112 begins expansion of the cooling fluid. From points "2" to "3", the ideal Stirling cycle is characterized by a reversible volume expansion. At point "3" the displacer 112 is in motion away from the piston 124 to provide an expansion space into which the cooling fluid can further expand. As will be appreciated, the expansion of the cooling fluid will further lower the cooling fluid temperature due to conversion of thermal to mechanical energy. At point "4" the piston 124 is in the same position as point "3" while the displacer 112 is at full expansion of the cooling fluid. From points "3" to "4" the ideal Stirling cycle is characterized by constant temperature expansion and reversible isothermal heat addition. From points "4" to "1" the displacer 112 and the piston 124 return to their initial positions effecting a reversible constant volume compression process. After that, a new cycle can begin.

Alternatively, other thermodynamic cycles can be employed. By way of example, the idealized Carnot and Brayton cycles depicted in FIGS. 4A and 4C, respectively, can be employed. "$T_r$" denotes temperatures where refrigeration is obtained. This is the lowest temperature for the ideal Carnot and Stirling cycles but not the lowest cycle temperature for the ideal Brayton cycle. The ideal Carnot cycle is characterized by constant temperature compression and reversible isothermal heat removal between points "1" and "2", constant entropy expansion between points "2" and "3", constant temperature expansion and reversible isothermal heat addition between points "3" and "4", and constant entropy compression between points "4" and "1". The ideal Brayton cycle is characterized by constant entropy compression from point "4" to point "1", constant pressure heat removal from point "1" to point "2", constant entropy expansion from point "2" to point "3", and constant pressure heat addition from point "3" to point "4"

The Brayton cycle is not as desirable thermodynamically as the Carnot, Ericsson and Stirling cycles. While the ratio of the required work input to the refrigeration produced are the same for the Carnot, Ericsson and Stirling cycles at all applied pressure ratios (i.e., source and sink temperatures), for the Brayton cycle without work recovery (which is the case for compact systems) the ratio of the required work input to the refrigeration is greater by approximately a factor of about 1.7, 2.3, and 3.1 at pressure ratios of 2, 4, and 8 respectively. The reason for this is that while the Carnot, Ericsson, and Stirling cycles provide the refrigeration at the required constant temperature levels (which is the requirement for condensation) the lowest temperature in the Brayton cycle must be considerably below that. Thus, for the compact cryocoolers there is an important potential advantage of low unit energy consumption.

There is another class of refrigerators, however, which may be advantageously applied because of its simplicity and reliability. These in general follow the so-called Hampson liquefier process where the temperature drop is achieved by isenthalpic expansion of the working fluid through throttling in a valve or capillary. In the miniature cryocooling units, however, a suitable mixture of refrigerants is applied thus decreasing the irreversibility of the throttling process.

Figure 5:
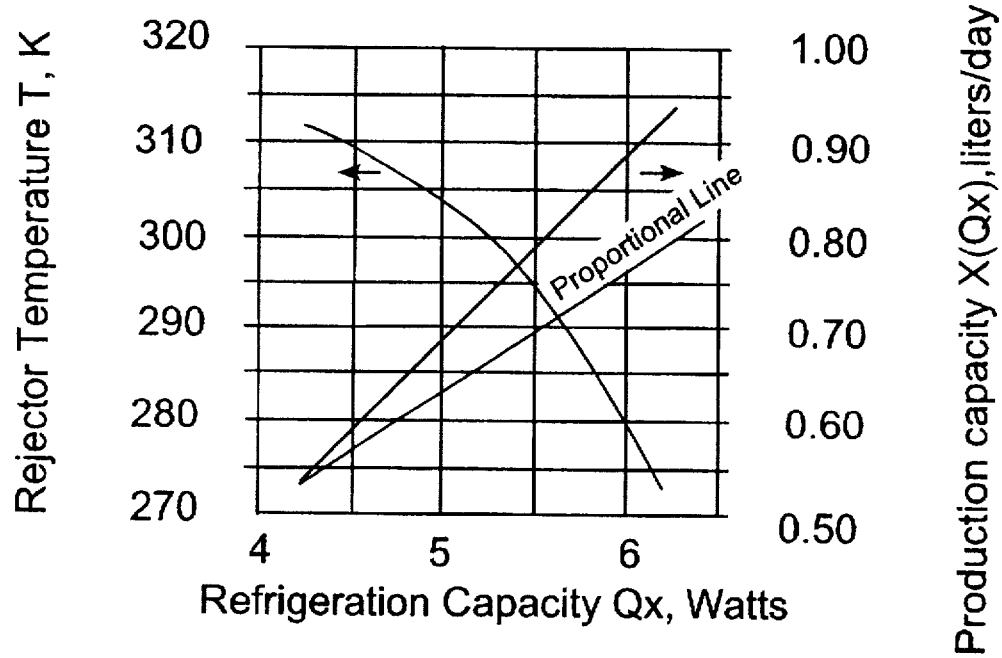
FIG. 5 is a plot of the relationship between cryocooler capacity and rejector temperature.

The refrigeration unit 140 has a significant impact on the cooling capacity of the cryocooler 22. FIG. 5 is a plot of heat rejector 120 temperature vs refrigeration capacity for the cryocooler 22. As can be seen from curve 150 of FIG. 5, as the heat rejector temperature decreases, the refrigeration capacity of the cryocooler increases. Likewise, as can be seen from curve 152 as the refrigeration capacity of the cryocooler increases, the production capacity also increases. In fact it increases over the proportional line.

The refrigeration unit 140 can be any suitable means for lowering the temperature of the heat rejector 120 and/or for maintaining continuously the temperature of the heat rejector 120 at a desired level. By way of example, the refrigeration unit 140 can be a conventional refrigerator, preferably of the vapor compression type. The cooling or maintaining of the temperature can be done either by convection or by direct thermal contact of the refrigerant with the heat rejector 120 via an external circuit of the refrigeration unit 140. The boiling surface (which may or may not be the heat rejector 120 surface) can be bare or treated by any of the known methods, e.g., mechanical activation, sintered porous surfaces, or by electrostatic methods to reduce the temperature difference between the boiling refrigerant and the boiling surface. The refrigerant preferably has a boiling point of no more than about 50° F., and more preferably ranging from about –45 to about +45° F., and most preferably ranging from about –30 to about +32° F. Alternatively, the heat rejector 120 can be cooled or maintained at a selected temperature by contacting the heat rejector 120 with a nonvaporizable cooling fluid, such as air or chilled water, having the selected temperature or a temperature slightly below the selected temperature.

High thermal resistance between the linear motor 128 and the heat rejector 120 is advantageous to cause the heat of compression but not the heat from the motor 128 to be removed by the refrigeration unit. The heat of the motor 128 is preferably removed by the heat rejection by the atmospheric air. To impede the heat conduction from the linear motor to the pre-cooling heat sink. The evaporator of the refrigeration unit may be placed inside of the cryocooler in close proximity and thermal communication of the warm end of the regenerator 108 and displacer 112.

The operation of the system will now be described with reference to FIGS. 1 and 2. An input gas 45, typically air, passes through the gas input 44 and is filtered by the filter 28 to provide the filtered gas 54. The filtered gas 54 is substantially free of particulate matter. The filtered gas 54 passes via conduit 46 and is compressed by the compression device 30 to form the compressed gas 58. The compressed gas 58 passes via conduit 50 to the separator 34 where molecular oxygen gas is separated from the compressed gas 58 to form the concentrated gas 42 and offgas 38. The concentrated gas 42 passes via conduit 26 through bypass valve 82a via conduit 160 to the user and bypass valve 82b via conduit 86 to the liquefier 62 in the desired ratio. The liquefier 62 condenses the concentrated gas 42 and the liquid oxygen is collected in the dewar 66. From the dewar 66, liquid oxygen can be dispensed into a portable containment vessel for placement on a stroller or a backpack to provide a patient with mobility.

Figure 6:
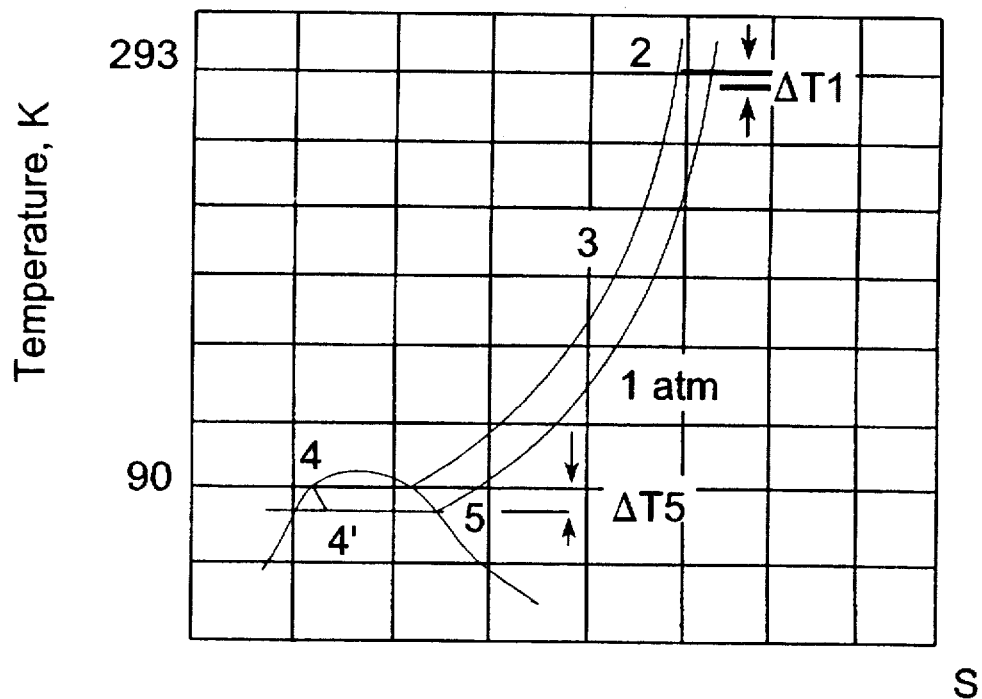
FIG. 6 is a plot of temperature vs entropy depicting the gas liquefication process.

The liquefication cycle of the oxygen is depicted in FIG. 6. The molecular oxygen in the concentrated gas 42 is at point "2" when it enters the cryogenic subsystem 18. Heat from the oxygen gas is transferred to the liquefier 62, and the gas is cooled to point "3". The cooled oxygen gas initially contacts the condensation surfaces on the liquefier 62 at point "3". Through sensible cooling of and latent heat removal from the cooled oxygen gas (as a result of contact with the condensation surfaces), the cooled oxygen gas moves from point "3" to point "4" forming liquid oxygen. From point "4" to point "4'" a pressure drop or throttling occurs. The liquid oxygen then drains from the condensation surfaces into the dewar 66. It should be understood that the pressure drop between point 4 and 4' may be very slight entailing nothing more than the pressure drop in the cold portion of the heat exchanger or may be more substantial taking advantage at least part of the delivery pressure of the concentrator unit.

Figure 7:
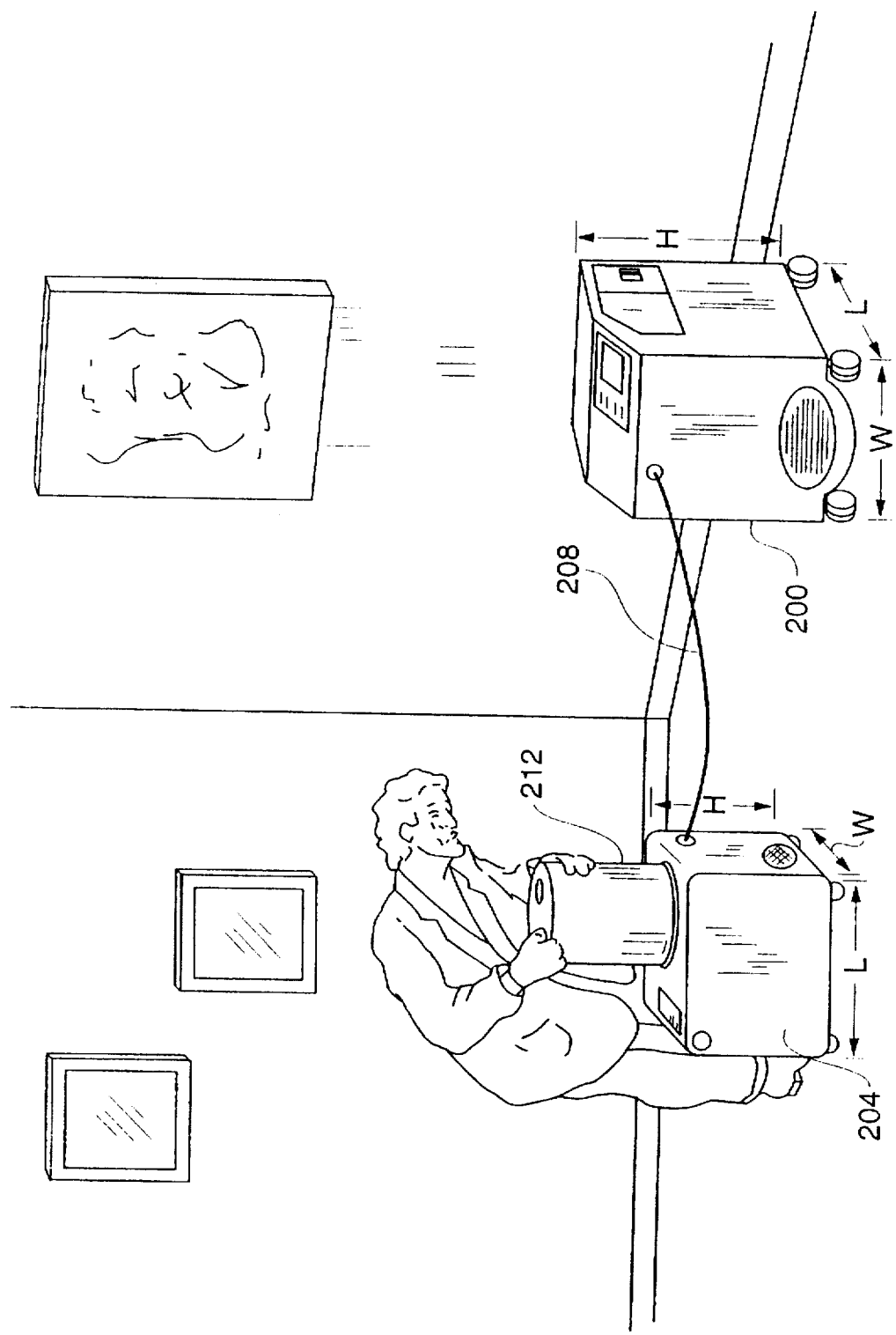
FIGS. 7 and 8 depict the use of the bimodular version of the system by a home oxygen patient.
Figure 8:
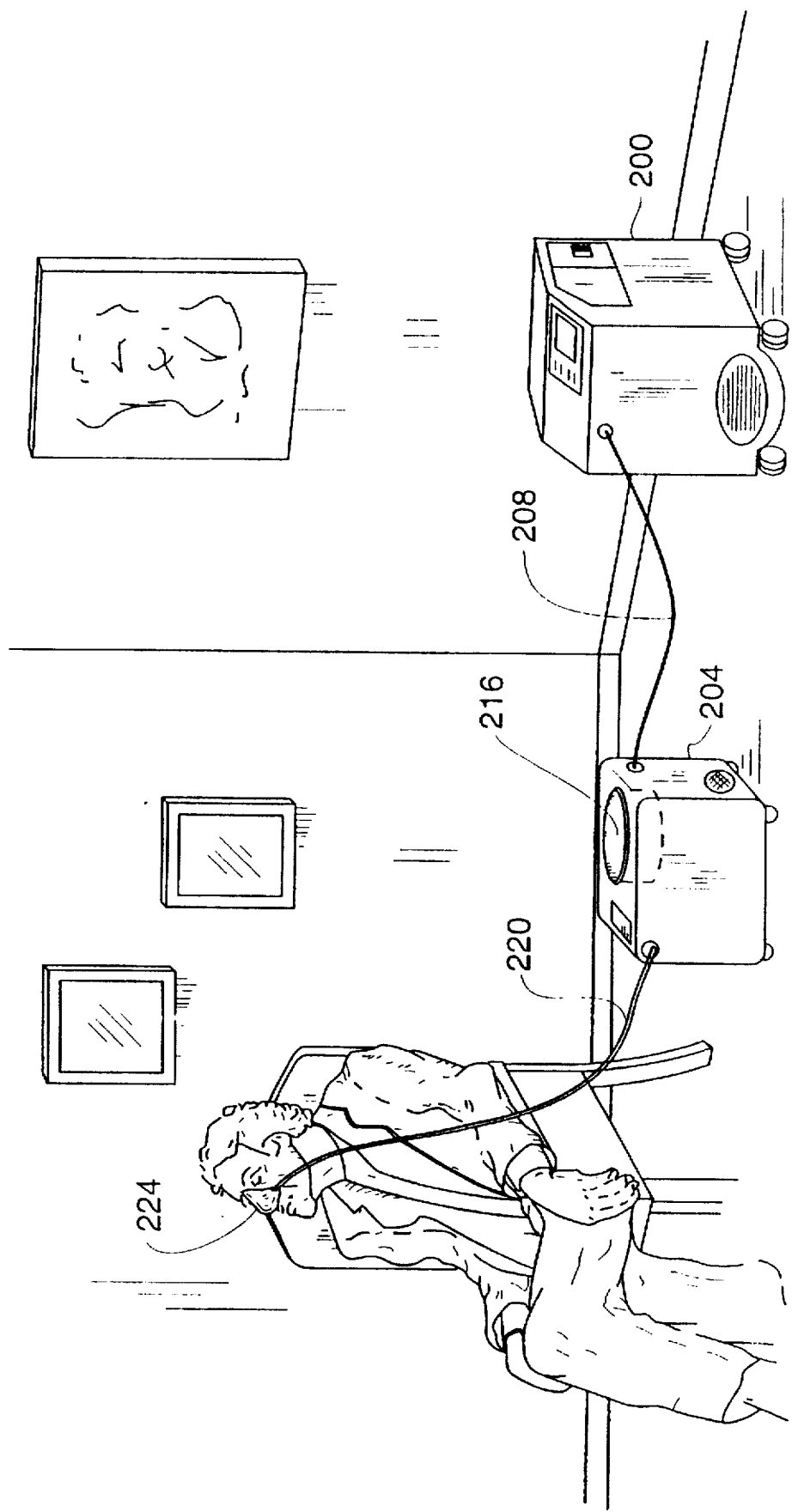

Referring to FIGS. 7 and 8, a bimodular version of the system is depicted in a home environment. The system includes the concentrator subsystem 14 in one housing 200 while the cryogenic subsystem 18 and cryocooler 22 are in a separate (nonintegral) housing 204. The concentrator subsystem 14 provides the concentrated (oxygen) gas 42 to the cryogenic subsystem 18 via connecting tube 208 (which is depicted as conduit 26 in FIG. 1). In one mode, a portable containment vessel 212 is received within an annulus 216 for charging of the vessel 212 with liquid oxygen. The vessel 212 can then be placed on a stroller or in a backpack to provide the user with a high degree of mobility. In another mode, the concentrated (oxygen) gas 42 can be dispensed directly to the patient via outlet tube 220.

The sizes of the two housings 200 and 204 are relatively compact providing for a high degree of portability. In this bimodular configuration, either housing has a maximum height ("H") of no more than about 28 inches a maximum width ("W") of no more than about 22 inches and a maximum length ("L") of no more than about 18 inches.

The high degree of portability of the system 10 permits the system to be readily located in an oxygen patient's home or residence, which can include a number of different facilities that the patient frequents, such as a long-term care facility, doctor's office and/or other care-related facility. Because the system can store liquid oxygen in the dewar (not shown in FIGS. 7 and 8) that is contained within the housing 204, the patient, while at home, can place the portable containment vessel 212 in the housing 204 which then dispenses oxygen from the dewar into the vessel 212. When the patient desires to remain stationary, he can place a breathing mask 224 connected to the outlet tube 220 to his mouth and nose and receive concentrated oxygen gas from the concentrator subsystem (by opening valve 82a (not shown in FIGS. 7 and 8)). The system has the ability to provide a portion of the concentrated oxygen to the patient and simultaneously produce liquid oxygen from a separate portion of the concentrated oxygen (i.e., by opening simultaneously valves 82a and 82b (not shown in FIGS. 7 and 8)).

As will be appreciated, the system can also be configured as a relatively compact and portable unimodular system in which all three subsystems, the concentrator subsystem, cryogenic subsystem, and cryocooler, are housed within a single (integrated) housing. In the unimodular version, the system has a maximum height ("H") of no more than about 40 inches, a maximum width ("W") of no more than about 24 inches and a maximum length ("L") of no more than about 30 inches.

While various embodiments of the present invention have been described in detail, it is apparent that modifications and adaptations of those embodiments will occur to those skilled in the art. By way of example, the system can be used to concentrate and liquefy gases other than oxygen, e.g., nitrogen, argon and refrigerants. However, it is to be expressly understood that such modifications and adaptations are within the scope of the present invention, as set forth in the following claims.

What is claimed is:

1. A method for producing and storing liquid oxygen in an oxygen patient's residence, comprising:

providing a liquid oxygen producing apparatus;

placing said liquid oxygen producing apparatus in a first location at which a first user of liquid oxygen resides;

producing liquid oxygen at said first location;

storing at said first location said liquid oxygen in a first container resulting from said producing step; and supplying oxygen to the first user from said first container.

2. A method, as claimed in claim 1, wherein:

said supplying step is conducted free of external delivery to said first location of any liquid oxygen that is used in performing said supplying step.

3. A method, as claimed in claim 1, wherein:

said storing step is conducted using at least portions of said liquid oxygen producing apparatus.

4. A method, as claimed in claim 1, wherein:

said supplying step is conducted at said first location.

5. A method, as claimed in claim 1, further including:

providing an oxygen concentrating apparatus at said first location and delivering gaseous oxygen to the user based on an oxygen output from said oxygen concentrator.

6. A method, as claimed in claim 5, wherein:

said delivering step is conducted while said liquid oxygen producing apparatus is producing said liquid oxygen.

7. A method for producing liquid oxygen in an oxygen patient's home, comprising:

separating oxygen from an oxygen-containing fluid by non-cryogenic means to form an oxygen-containing feedstream and an oxygen-depleted waste gas; and cryocooling at least a portion of the oxygen-containing feedstream to form liquid oxygen.

8. The method of claim 7, wherein the oxygen-containing fluid comprises at least one of water vapor, carbon dioxide, and nitrogen and the separating step comprises:

absorbing the at least one of water vapor, carbon dioxide, and nitrogen onto an absorbing substance at a first pressure to produce the oxygen-containing feedstream; and desorbing the at least one of water vapor, carbon dioxide, and nitrogen from the absorbing substance at a second pressure to produce the oxygen-depleted waste gas.

9. The method of claim 7, wherein the first pressure is more than the second pressure.

10. The method of claim 7, wherein the nitrogen-absorbing substance is a molecular sieve selected from the group consisting of zeolites, or carbon, and mixtures thereof.

11. The method of claim 7, wherein the separating step comprises:

filtering the oxygen-containing fluid to form the oxygen-depleted waste gas on a first, higher pressure side of the filter and the oxygen-containing feedstream gas on a lower pressure, opposing, second side of the filter.

12. The method of claim 11, wherein the oxygen-depleted waste gas has a first pressure on the first side of the filter and the oxygen-containing feedstream has a second pressure on the second side of the filter and the first pressure exceeds the second pressure.

13. The method of claim 11, wherein the separating step comprises:

applying a voltage to the filter to form opposing electrical polarities on the first and second sides of the filter.

14. The method of claim 7, wherein the cryocooling step is performed by a cryocooler having a heat rejection portion for discharging heat generated by the cryocooler and further comprising:

cooling the heat rejection portion or near the heat rejection portion of the cryocooler.

15. The method of claim 14, wherein the cooling step comprises:

contacting the heat rejection portion with a cooling fluid.

16. The method of claim 14, wherein the cooling step comprises:

refrigerating the heat rejection portion by at least one of evaporation and boiling of a refrigerant.

17. An apparatus for producing liquid oxygen in an oxygen patient's home, comprising:

non-cryogenic separating means for separating oxygen from an oxygen-containing fluid to form an oxygen-containing feedstream and an oxygen-depleted waste gas; and cryocooling means, in communication with the separating means, for cryocooling at least a portion of the oxygen-containing feedstream to form liquid oxygen.

18. The apparatus of claim 17, further comprising:

cooling means for cooling a heat rejection member or near the heat rejection member of the cryocooling means.

19. The apparatus of claim 17, further comprising:

compressing means, in communication with the separating means, for compressing an oxygen-containing input gas to form the oxygen-containing fluid and heat of compression.

20. The apparatus of claim 18, further comprising:

heat exchange means, in communication with the separating means, for dissipating the heat of compression.

21. The apparatus of claim 18, further comprising:

filtration means, in communication with the compressing means, for filtering the oxygen-containing input gas to remove particulate material therefrom.

22. The apparatus of claim 17, further comprising:

valve means, located between the separating means and the cryocooling means, for removing a portion of the oxygen-containing feedstream for inhalation by a patient.

23. The apparatus of claim 17, wherein:

the oxygen-containing feedstream is a gas and wherein the cryocooling means includes condensation surfaces for condensing the oxygen-containing fluid to form the liquid oxygen.

24. In an apparatus for producing liquid oxygen in an oxygen patient's home, a cryocooler, comprising:

compressing means for compressing a cryocooling fluid to form a compressed cryocooling fluid and heat of compression;

expansion means, in fluid communication with the compressing means, for expanding the compressed cryocooling fluid with or without work recovery to form an expanded, cold cryocooling fluid;

regenerating means, in fluid communication with the colder and warmer gas of the cooler;

a cold head, in fluid communication with the expansion means, such that the expanded, cold cryocooling fluid thermally contacts the cold head;

heat rejection means for dissipating the heat of compression; and refrigeration means for cooling the heat rejection means or near the heat rejection means below ambient temperature, thereby facilitating the dissipation of the heat of compression.

* * * * *